(12) United States Patent
Wang et al.

(10) Patent No.: US 10,189,758 B2
(45) Date of Patent: *Jan. 29, 2019

(54) METHOD FOR PRODUCING HYDROFLUOROOLEFIN

(71) Applicant: AGC Inc., Chiyoda-ku (JP)

(72) Inventors: Xu Wang, Chiyoda-ku (JP); Shinji Terazono, Chiyoda-ku (JP); Yuki Hayasaka, Chiyoda-ku (JP); Toshio Suzuki, Chiyoda-ku (JP); Satoshi Kawaguchi, Chiyoda-ku (JP); Mitsugu Kasagawa, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,310

(22) Filed: Jun. 1, 2017

(65) Prior Publication Data

US 2017/0267613 A1   Sep. 21, 2017

Related U.S. Application Data

(63) Continuation of application No. PCT/JP2015/083811, filed on Dec. 1, 2015.

(30) Foreign Application Priority Data

Dec. 5, 2014   (JP) ................................ 2014-246810

(51) Int. Cl.
*C07C 17/23* (2006.01)
*B01J 23/52* (2006.01)
(Continued)

(52) U.S. Cl.
CPC .............. *C07C 17/23* (2013.01); *B01J 21/18* (2013.01); *B01J 23/44* (2013.01); *B01J 23/52* (2013.01);
(Continued)

(58) Field of Classification Search
CPC ............................ C07C 17/23; C07C 17/354
See application file for complete search history.

(56) References Cited

U.S. PATENT DOCUMENTS 8,318,991 B2 * 11/2012 Sugimoto ............... C07C 17/23
570/153
8,530,710 B2 * 9/2013 Takagi .................... C07C 17/23
570/176
(Continued)

FOREIGN PATENT DOCUMENTS

CA        2015247 A1 * 10/1997
EP     3 187 477 A1    7/2017
(Continued)

OTHER PUBLICATIONS

International Search Report dated Feb. 16, 2016 in PCT/JP2015/083811, filed on Dec. 1, 2015.

*Primary Examiner* — Medhanit W Bahta
(74) *Attorney, Agent, or Firm* — Oblon, McClelland, Maier & Neustadt, L.L.P.

(57) ABSTRACT

To provide a method for producing a hydrofluoroolefin, wherein formation of an over-reduced product having hydrogen added to an aimed hydrofluorolefin and an over-reduced product having some of fluorine atoms in the aimed product replaced with hydrogen atoms, as by-products, is suppressed.
A method for producing a hydrofluoroolefin, which comprises reacting a specific chlorofluoroolefin with hydrogen in the presence of a catalyst supported on a carrier, to obtain a specific hydrofluoroolefin, wherein the catalyst is a catalyst composed of particles of an alloy containing at least one platinum group metal selected from the group consisting of palladium and platinum, and gold, and the proportion of the gold at the surface of the alloy particles is from 5 to 30 mass (Continued)

% per 100 mass % in total of the platinum group metal and the gold at the surface of the alloy particles.

20 Claims, 1 Drawing Sheet

(51) Int. Cl.
  *B01J 21/18* (2006.01)
  *B01J 23/44* (2006.01)
  *B01J 35/00* (2006.01)
  *B01J 35/02* (2006.01)
  *B01J 37/08* (2006.01)

(52) U.S. Cl.
  CPC ....... *B01J 35/0006* (2013.01); *B01J 35/0073* (2013.01); *B01J 35/026* (2013.01); *B01J 37/08* (2013.01)

(56) References Cited

U.S. PATENT DOCUMENTS

| | | |
|---|---|---|
| 2011/0251442 A1 | 10/2011 | Okamoto et al. |
| 2011/0319676 A1 | 12/2011 | Takagi et al. |
| 2011/0319678 A1 | 12/2011 | Seki et al. |
| 2011/0319680 A1 | 12/2011 | Kawaguchi et al. |
| 2011/0319681 A1 | 12/2011 | Kawaguchi et al. |
| 2013/0131402 A1* | 5/2013 | Millefanti ................ B01J 21/18 570/156 |

FOREIGN PATENT DOCUMENTS

| | | |
|---|---|---|
| EP | 3 187 478 A1 | 7/2017 |
| JP | 1-287044 | 11/1989 |
| JP | 2-286635 | 11/1990 |
| JP | 5582036 | 9/2014 |
| JP | 5713016 | 5/2015 |
| JP | 5713017 | 5/2015 |
| JP | 5713018 | 5/2015 |
| JP | 5786858 | 9/2015 |
| WO | WO 2008/060614 A2 | 5/2008 |
| WO | WO 2010/074254 A1 | 7/2010 |
| WO | WO 2011/162336 A1 | 12/2011 |
| WO | WO 2011/162337 A1 | 12/2011 |
| WO | WO 2011/162338 A1 | 12/2011 |
| WO | WO 2011/162339 A1 | 12/2011 |
| WO | WO 2012/000853 A1 | 1/2012 |

* cited by examiner

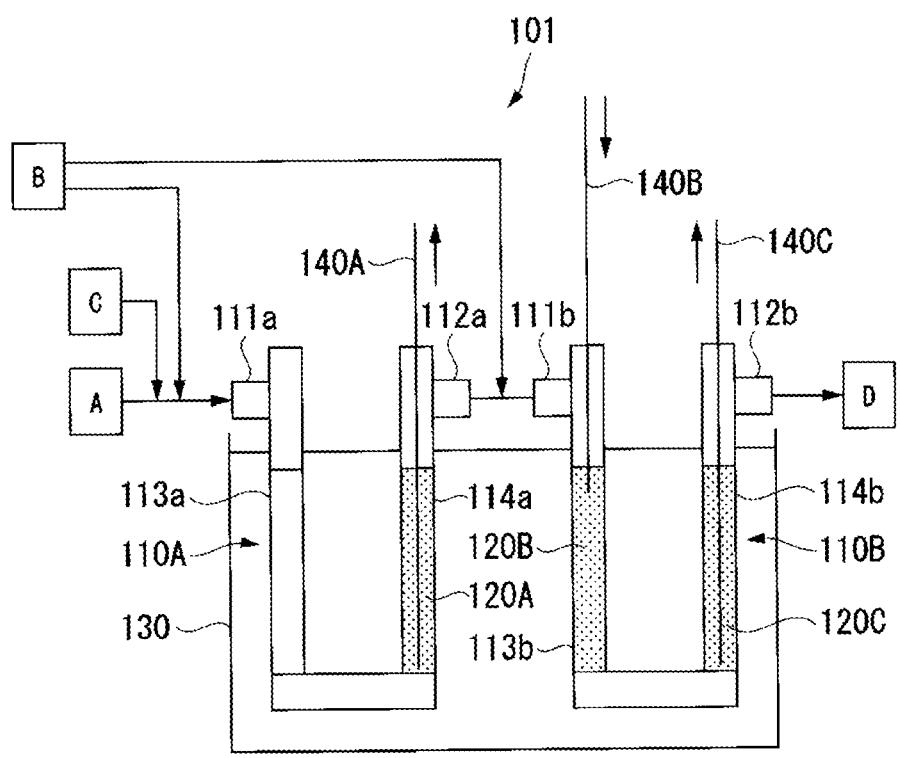

METHOD FOR PRODUCING HYDROFLUOROOLEFIN

TECHNICAL FIELD

The present invention relates to a method for producing a hydrofluoroolefin.

BACKGROUND ART

A hydrofluoroolefin such as 2,3,3,3-tetrafluoropropene ($CF_3CF=CH_2$) (hereinafter sometimes referred to as "HFO-1234yf) is useful as an alternative compound to a chlorofluorocarbon to be used as a refrigerant, etc., since the hydrofluoroolefin contains no chlorine atom.

As a method for producing the hydrofluoroolefin, for example, the following methods (i) to (iv) have been proposed.

(i) A method of subjecting 1,1-dichloro-2,2,3,3,3-pentafluoropropane ($CF_3CF_2CHCl_2$) (hereinafter sometimes referred to as "HCFC-225ca") to a dehydrofluorination reaction to obtain 1,1-dichloro-2,3,3,3-tetrafluoropropene ($CF_3CF=CCl_2$) (hereinafter sometimes referred to as "CFO-1214ya"), and then reacting CFO-1214ya with hydrogen as represented by the following formula (6) in the presence of a palladium catalyst supported on alumina to obtain HFO-1234yf (Patent Document 1).

$$CF_3CF=CCl_2+2H_2\rightarrow CF_3CF=CH_2+2HCl \quad (6)$$

(ii) A method of subjecting $RfCF=CX_2$ (wherein Rf is a $C_{1-10}$ fluoroalkyl group, and X is a chlorine atom, a bromine atom or an iodine atom) and hydrogen to a reaction as represented by the following formula (9) in the presence of a palladium catalyst supported on activated carbon to obtain $RfCF=CH_2$ (Patent Document 2).

$$RfCF=CX_2+2H_2\rightarrow RfCF=CH_2+2HX \quad (9)$$

(iii) A method of subjecting chlorotrifluoroethylene and hydrogen to a reaction as represented by the following formula (10) in the presence of a palladium catalyst supported on activated carbon to obtain a trifluoroethylene. (Patent Document 3).

$$CF_2=CClF+H_2\rightarrow CF_2=CHF+HCl \quad (10)$$

(iv) A method of subjecting 1,2-dichlorodifluoroethylene and hydrogen to a reaction as represented by the following formula (11) in the presence of a palladium catalyst supported on activated carbon (Patent Document 4).

$$CClF=CClF+2H_2\rightarrow CHF=CHF+2HCl \quad (11)$$

However, in the method (i), 1,1,1,1,2-tetrafluoropropane ($CF_3CHFCH_3$) (hereinafter sometimes referred to as "HFC-254eb") which is an over-reduced product having hydrogens added to HFO-1234yf and 3,3,3-trifluoropropene ($CF_3CH=CH_2$) (hereinafter sometimes referred to as "HFO-1243zf") which is an over-reduced product having some of fluorine atoms in HFO-1234yf replaced by hydrogen atoms, are formed as by-products.

If the over-reduced product is formed in a large amount, the yield of the aimed product decreases, and the production efficiency decreases. Further, HFO-1243zf has a boiling point close to that of the aimed HFO-1234yf, and is thereby hardly separated and removed by subsequent distillation. Accordingly, if a large amount of HFO-1234zf is by-produced, HFO-1243zf will remain as an impurity in HFO-1234yf obtainable by distillation. In such a case, a separation and purification step is additionally required to obtain high purity HFO-1234yf.

Also in the method (ii), $RfCHFCH_3$ and $RfCH=CH_2$ which are over-reduced products are formed as by-products together with the aimed $RfCF=CH_2$. In a case where Rf is $CF_3$—, that is, in a case where the aimed product is HFO-1234yf, the production efficiency of HFO-1234yf decreases, and a separation and purification step is additionally required to obtain high purity HFO-1234yf, in the same manner as in the method (i).

Also in the methods (iii) and (iv), in addition to the aimed product, an over-reduced product is formed as a by-product, whereby the production efficiency of the aimed product decreases, and the purity of the aimed product decreases.

PRIOR ART DOCUMENTS

Patent Documents

Patent Document 1: WO2008/060614
Patent Document 2: JP-A-H2-286635
Patent Document 3: WO2012/000853
Patent Document 4: JP-A-H1-287044

DISCLOSURE OF INVENTION

Technical Problem

It is an object of the present invention to provide a method for producing a hydrofluoroolefin, wherein when replacing chlorine atoms in chlorofluoroolefin as raw material by hydrogen atoms to produce a hydrofluoroolefin, an over-reduced product having hydrogen added to the aimed hydrofluoroolefin and an over-reduced product having some of fluorine atoms in the aimed product replaced by hydrogen atoms are less likely to be formed as by-products.

Solution to Problem

The present invention provides the followings.

[1] A method for producing a hydrofluoroolefin, which comprises reacting a chlorofluoroolefin represented by the following formula (1) with hydrogen in the presence of a catalyst supported on a carrier, to obtain a hydrofluoroolefin represented by the following formula (2), wherein the catalyst is composed of particles of an alloy comprising at least one platinum group metal selected from the group consisting of palladium and platinum, and gold, and the proportion of the gold at the surface of the alloy particles is from 5 to 30 mass % per 100 mass % in total of the platinum group metal and the gold at the surface of the alloy particles:

$$CZX=CClY \quad (1)$$

wherein X is a fluorine atom or a chlorine atom, Y is a fluorine atom, a chlorine atom or a hydrogen atom, and Z is a fluorine atom or $CF_3$;

$$CZX'=CHY' \quad (2)$$

wherein X' is a fluorine atom when X is a fluorine atom, or X' is a hydrogen atom when X is a chlorine atom, Y' is a fluorine atom when Y is a fluorine atom, or Y' is a hydrogen atom when Y is a chlorine atom or a hydrogen atom, and Z is the same as Z in the formula (1).

[2] The method for producing a hydrofluoroolefin according to [1], wherein the proportion of the gold at the surface of the alloy particles is from 5 to 20 mass % per 100 mass % in total of the platinum group metal and the gold at the surface of the alloy particles.

[3] The method for producing a hydrofluoroolefin according to [1], wherein the proportion of the gold at the surface of the alloy particles is from 5 to 15 mass % per 100 mass % in total of the platinum group metal and the gold at the surface of the alloy particles.

[4] The method for producing a hydrofluoroolefin according to any one of [1] to [3], wherein the catalyst is composed of alloy particles of a palladium-gold alloy.

[5] The method for producing a hydrofluoroolefin according to any one of [1] to [4], wherein the carrier is at least one member selected from the group consisting of activated carbon, carbon black and carbon fibers.

[6] The method for producing a hydrofluoroolefin according to any one of [1] to [4], wherein the carrier is activated carbon.

[7] The method for producing a hydrofluoroolefin according to any one of [1] to [4], wherein the carrier is at least one member selected from the group consisting of alumina, silica, titania and zirconia.

[8] The method for producing a hydrofluoroolefin according to any one of [1] to [7], wherein the amount of the alloy particles supported is from 0.1 to 10 parts by mass based on 100 parts by mass of the carrier.

[9] The method for producing a hydrofluoroolefin according to any one of [1] to [8], wherein the chlorofluoroolefin and hydrogen are introduced to a catalyst layer packed with the carrier supporting the catalyst, and reacted in a gaseous phase.

[10] The method for producing a hydrofluoroolefin according to [9], wherein the chlorofluoroolefin and hydrogen are introduced to a gas introduction part of the catalyst layer, and, at the same time, hydrogen is introduced from at least one point between the gas introduction part and a gas discharge part of the catalyst layer.

[11] The method for producing a hydrofluoroolefin according to [9] or [10], wherein the temperature of the region at the highest temperature in the catalyst layer packed with the carrier supporting the catalyst is at least 90° C.

[12] The method for producing a hydrofluoroolefin according to any one of [1] to [8], wherein the chlorofluoroolefin and hydrogen are reacted in a liquid phase in the presence of the carrier supporting the catalyst.

[13] The method for producing a hydrofluoroolefin according to any one of [1] to [12], wherein the ratio ($H_2$/Cl) of the number of moles of hydrogen to the number of moles of chlorine atoms in the chlorofluoroolefin is from 0.1 to 0.7.

[14] The method for producing a hydrofluoroolefin according to any one of [1] to [13], wherein the chlorofluoroolefin is at least one member selected from the group consisting of chlorotrifluoroethylene, (E)-1,2-dichloro-1,2-difluoroethylene, (Z)-1,2-dichloro-1,2-difluoroethylene, 1,1-dichloro-2,3,3,3-tetrafluoropropene and 1-chloro-2,3,3,3-tetrafluoropropene.

[15] The method for producing a hydrofluoroolefin according to any one of [1] to [14], wherein the chlorofluoroolefin is 1,1-dichloro-2,3,3,3-tetrafluoropropene, and the hydrofluoroolefin is 2,3,3,3-tetrafluoropropene.

Advantageous Effects of Invention

According to the method for producing a hydrofluoroolefin of the present invention, when producing a hydrofluoroolefin by replacing chlorine atoms in chlorofluoroolefin as raw material by hydrogen atoms, an over-reduced product having hydrogen added to the aimed hydrofluoroolefin and an over-reduced product having some of fluorine atoms in the aimed product replaced by hydrogen atoms, are less likely to be formed as by-products.

BRIEF DESCRIPTION OF DRAWING

The FIGURE is a schematic diagram illustrating a reaction apparatus used in Examples.

DESCRIPTION OF EMBODIMENTS

[Method for Producing Hydrofluoroolefin]

The method for producing a hydrofluoroolefin of the present invention is a method of reacting a specific chlorofluoroolefin with hydrogen in the presence of a specific catalyst supported on a carrier to produce the aimed hydrofluoroolefin.

(Chlorofluoroolefin)

The chlorofluoroolefin which is one of the raw materials in the present invention is a compound represented by the formula (1).

In the compound represented by the formula (1), depending on selection of X, Y and Z, a transform (hereinafter referred to also as "E form") and a cis form (hereinafter referred to also as "Z form") may be present, but in the present specification, the compound may be any one of E form, Z form and a mixture of E/Z forms, unless it is specifically identified to be E form or Z form. The same applies to other compounds having a carbon-carbon double bond.

Hereinafter, among geometric isomers, a trans-form will be represented by adding the prefix (E) to a compound name or a chemical formula, and a cis-form will be represented by adding the prefix (Z) to a compound name or a chemical formula.

As the chlorofluoroolefin represented by the formula (1) as raw material for the production method of the present invention, it is possible to use a compound wherein the combination of X, Y and Z is one type, or to use compounds wherein said combination is two or more types. However, it is preferred to select the combination of compounds represented by the formula (1) so that the structure of a compound represented by the formula (2) to be formed would be the same.

Among them, as the chlorofluoroolefin, chlorotrifluoroethylene, (E)-1,2-dichloro-1,2-difluoroethylene, (Z)-1,2-dichloro-1,2-difluoroethylene, CFO-1214ya, 1-chloro-2,3,3,3-tetrafluoropropene (hereinafter referred to also as "HCFO-1224yd") or a mixture of CFO-1214ya and HCFO-1224yd is preferred, from the viewpoint of obtaining a hydrofluoroolefin which is expected to be an environmentally friendly alternative refrigerant having a high refrigerating efficiency.

Chlorotrifluoroethylene can be produced by subjecting 1,1,2-trichloro-1,2,2-trifluoroethane to a dechlorination reaction or subjecting chlorodifluoromethane and dichlorofluoromethane to a heat decomposition reaction.

(E)-1,2-dichloro-1,2-difluoroethylene and (Z)-1,2-dichloro-1,2-difluoroethylene can be produced by subjecting dichlorofluoromethane to a heat decomposition reaction.

CFO-1214ya can be produced by a known method. As the known method, a method of subjecting HCFC-225ca to a dehydrofluorination reaction may be mentioned. The dehydrofluorination reaction may, for example, be carried out by bringing HCFC-225ca into contact with an aqueous alkali solution in the presence of a phase transfer catalyst. For the reaction, dichloropentafluoropropane (hereinafter sometimes referred to as "HCFC-225") containing HCFC-225ca may be used. In the case of using HCFC-225, only HCFC- 225ca contained in HCFC-225 is selectively subjected to the dehydrofluorination by the phase transfer catalyst. After the reaction, CFO-1214ya can be separated and recovered by a known method such as distillation.

HCFC-225 can be produced by reacting tetrafluoroethylene and dichlorofluoromethane in the presence of a catalyst such as aluminum chloride. HCFC-225 obtained by the reaction contains as the main components HCFC-225ca and 1,3-dichloro-1,2,2,3,3-pentafluoropropane ($CHClCF_2CClF_2$) (hereinafter sometimes referred to as "HCFC-225cb") and further contains a small amount of 2,2-dichloro-1,1,3,3,3-pentafluoropropane ($CHF_2CCl_2CF_3$), 2,3-dichloro-1,1,2,3,3-pentafluoropropane ($CHF_2CClFCClF_2$), etc.

As HCFC-225, a commercial product may be used. As a commercial product, ASAHIKLIN (trademark) AK225 (manufactured by Asahi Glass Company, Limited, a mixture comprising 48 mol % of HCFC-225ca and 52 mol % of HCFC-225cb) may, for example, be mentioned.

The phase transfer catalyst is preferably tetrabutylammonium bromide (hereinafter sometimes referred to as "TBAB").

HCFO-1224yd is formed as an intermediate when CFO-1214ya and hydrogen are reacted to obtain HFO-1234yf.

(Hydrofluoroolefin)

The hydrofluoroolefin as the aimed product in the production method of the present invention is a compound represented by the formula (2).

As described above, the types of X', Y' and Z in the formula (2) have correspondence relationship to the types of X, Y and Z in the formula (1).

In a case where the chlorofluoroolefin is chlorotrifluoroethylene, the hydrofluoroolefin as the aimed product is trifluoroethylene obtained by the reaction represented by the following formula (3):

$$CFCl=CF_2+H_2 \rightarrow CHF=CF_2+HCl \quad (3)$$

In the production method of the present invention, the arrangement E/Z to the carbon-carbon double bond in the compound represented by the formula (1) may be kept or may not be kept. Accordingly, the compound represented by the formula (2) to be formed may be any of E-form, Z-form and a mixture of E/Z forms.

In a case where the chlorofluoroolefin is the E-form and/or the Z-form of 1,2-dichloro-1,2-difluoroethylene, the reaction proceeds while the E/Z is kept. That is, as the reaction of E-form as raw material, the reaction represented by the following formula (4) proceeds, and as the reaction of Z-form as raw material, the reaction represented by the following formula (5) proceeds, whereby as the hydrofuloroolefin as the aimed product, the corresponding E-form or Z-form compound can be obtained. Further, in the reaction of an E/Z mixture as raw material, either one or both of the reactions represented by the formula (4) and the formula (5) proceed, whereby E-form, Z-form or a mixture of E/Z forms of 1,2-difluoroethylene can be obtained.

$$(E)\text{-}CFCl=CFCl+2H_2 \rightarrow (E)\text{-}CHF=CHF+2HCl \quad (4)$$

$$(Z)\text{-}CFCl=CFCl+2H_2 \rightarrow (Z)\text{-}CHF=CHF+2HCl \quad (5)$$

In a case where the chlorofluoroolefin is CFO-1214ya, the aimed hydrofluoroolefin is HFO-1234yf to be obtained by the reaction represented by the following formula (6).

$$CF_3CF=CCl_2+2H_2 \rightarrow CF_3CF=CH_2+2HCl \quad (6)$$

In a case where the chlorofluoroolefin is HCFO-1224yd, the aimed hydrofluoroolefin is HFO-1234yf to be obtained by the reaction represented by the following formula (7).

$$CF_3CF=CHCl+H_2 \rightarrow CF_3CF=CH_2+HCl \quad (7)$$

(Catalyst)

The catalyst in the present invention is composed of particles of an alloy comprising at least one platinum group metal selected from the group consisting of palladium and platinum (hereinafter sometimes referred to as "Pd/Pt metal"), and gold, and the alloy particles are supported on a carrier. Further, the carrier supporting the alloy particles is sometimes referred to as "catalyst-supporting carrier" hereinafter.

The amount of the alloy particles supported on the catalyst-supporting carrier is preferably from 0.1 to 10 parts by mass, more preferably from 0.5 to 1 part by mass, per 100 parts by mass of the carrier. When the amount of the alloy particles supported is at least the above lower limit value, the reactivity of the chlorofluoroolefin and hydrogen will improve. When the amount of the alloy particles supported is at most the above upper limit value, the excessive temperature increase of the catalyst layer by the heat of reaction will be suppressed, and the formation of an over-reduced product as a by-product tends to be suppressed, and in addition, the catalyst will readily be available.

In the reaction of the present invention, the amount of by-products to be formed in the products is preferably from 0 to 10 mol %, per the total formed products.

The alloy in the alloy particles may contain an additive element in addition to the Pd/Pt metal and gold. The additive element may, for example, be manganese, copper, aluminium, lithium, sodium, potassium, magnesium, silver, zinc, cadmium, indium, silicon, germanium, tin, lead, arsenic, antimonium, bismuth, iron, cobalt or nickel. Further, the additive element may be supported on a carrier independent of the alloy particles. The additive element may be one type, or two or more types may be used.

The amount of the additive element is preferably from 0.01 to 20 parts by mass, per 100 parts by mass in total of the Pd/Pt metal and gold.

The specific surface area of the catalyst-supporting carrier is preferably from 10 to 2,000 m²/g, more preferably from 100 to 1,500 m²/g. When the specific surface area of the catalyst-supporting carrier is at least the above lower limit value, the reactivity of the chlorofluoroolefin and hydrogen will improve. When the specific surface area of the catalyst-supporting carrier is at most the above upper limit value, the formation of an over-reduced product as a by-product tends to be further suppressed.

The specific surface area of the catalyst-supporting carrier is measured in accordance with the $N_2$ gas absorption method, for example, the BET method.

<Alloy Particles>

The alloy constituting the alloy particles is one formed by alloying the Pd/Pt metal and gold. The alloy particles are formed on a carrier at the time of alloying by heat treatment or the like.

In a case where the catalyst composed of the Pd/Pt metal is used, the hydrogen-reduction activity of the Pd/Pt metal is too high, and thereby an over-reduced product tends to be by-produced. Thus, the Pd/Pt metal is alloyed with gold which hardly reacts with hydrogen to lower the hydrogen-reduction activity of the Pd/Pt metal, whereby the formation of an over-reduced product as a by-product is suppressed. Further, by forming into an alloy, the durability of the catalyst is improved.

In a case where either one of palladium and platinum is used at the time of alloying with gold, palladium or platinum is formed into an alloy with gold.

In a case where both palladium and platinum are used at the time of alloying with gold, palladium and platinum may be in the form of a mixture or may be in the form of an alloy. There are a case where palladium and gold are used in the form of a mixture, a case where palladium and gold are formed into an alloy, a case where platinum and gold are formed into an alloy, and a case where palladium, platinum and gold are formed into an alloy. In the present specification, both one having a palladium-platinum alloy alloyed with gold and one having the mixture of palladium and platinum alloyed with gold are used as a palladium-platinum-gold alloy.

Palladium has a high conversion rate and selectivity to the hydrogen reduction reaction. Thus, as the Pd/Pt metal, palladium is preferred. Further, platinum has a high acid durability and a long catalyst life span. Thus, from the viewpoint of obtaining all of these features of palladium and platinum, at the time of forming an alloy, as the Pd/Pt metal, both palladium and platinum are preferably used, and a palladium-platinum alloy is more preferably used.

Palladium and platinum are preferably alloyed by heat treatment under an atmosphere of an inert gas (such as nitrogen gas or argon gas) or under a reduction atmosphere containing a slight amount of hydrogen. By alloying under such an atmosphere, palladium and platinum are alloyed in a more uniform state, whereby the effect to suppress the formation of an over-reduced product as a by-product and the durability of the catalyst are more improved.

The heating temperature at the time of forming an alloy is preferably from 150 to 600° C., more preferably from 300 to 550° C.

The heating time at the time of forming an alloy is preferably from 1 to 24 hours, more preferably from 3 to 9 hours.

The mass ratio of palladium to platinum at the time of forming an alloy is usually preferably from 60/40 to 99/1, more preferably from 80/20 to 95/5. Within this range, the high selectivity and the long life span of the catalyst can be both established.

The Pd/Pt metal and gold are preferably alloyed by heat treatment under an atmosphere of an inert gas (such as nitrogen gas or argon gas) or under a reduction atmosphere containing a slight amount of hydrogen. By alloying under such an atmosphere, the Pd/Pt metal and gold are alloyed in a more uniform state, whereby the effect to suppress the formation of an over-reduced product as a by-product and the durability of the catalyst are more improved.

The heating temperature at the time of forming an alloy is preferably from 150 to 600° C., more preferably from 300 to 550° C.

The heating time at the time of forming an alloy is preferably from 1 to 24 hours, more preferably from 3 to 9 hours.

The mass ratio of the Pd/Pt metal to gold at the time of forming an alloy is usually preferably from 60/40 to 99/1, more preferably from 80/20 to 95/5, most preferably from 90/10 to 95/5. Within this range, it is easy to control the proportion of gold at the surface of the alloy particles to from 5 to 30 mass %.

The proportion of gold at the surface of the alloy particles is from 5 to 30 mass %, preferably from 5 to 20 mass %, more preferably from 5 to 15 mass %, per 100 mass % in total of the Pd/Pt metal and gold at the surface of the alloy particles. When the proportion of gold at the surface of the alloy particles is at least the above lower limit value, an over-reduced product as a by-product is less likely to be formed. When the proportion of gold at the surface of the alloy particles is at most the above upper limit value, the conversion rate can be maintained without lowering the activity of the Pd/Pt metal.

The proportion of gold at the surface of the alloy particles is obtained by the after-mentioned X-ray photoelectron spectroscopy (XPS) analytical method.

Further, the XPS quantitative analytical method is a method of irradiating a sample with X-ray and measuring photoelectron energy emitted from the sample. The XPS quantitative analytical method is used as an effective method for analyzing an element at a depth of about tens Å from the surface of a solid sample and analyzing the bonding state of an element, and the quantity of various types of elements can be simply measured.

The proportion of gold at the surface of the alloy particles is, for example, controlled by the following method.

(I) A method of adjusting the mass ratio of the Pd/Pt metal to gold or the heating temperature and the heating time at the time of supporting the Pd/Pt metal and gold simultaneously on a carrier and carrying out heat treatment to prepare alloy particles.

(II) An method of adjusting the mass ratio of the Pd/Pt metal to gold or the heating temperature and the heating time at the time of supporting the Pd/Pt metal or gold on a carrier, supporting the other component thereon and carrying out heat treatment to prepare alloy particles.

<Carrier>

The carrier is used to dispersedly support the alloy.

The carrier may, for example, be a carbon material (such as activated carbon, carbon black or carbon fibers), or an oxide-based material (such as alumina, silica, titania or zirconia). Preferred is activated carbon or alumina, which has a relatively large specific surface area and which readily support the alloy As the activated carbon, for example, activated carbon prepared from wood, charcoal, fruit shell such (as coconut shell), peat, lignite, coal or the like may be mentioned.

As the shape of the activated carbon, aggregates of briquette with a length at a level of from 2 to 5 mm, shot at a level of from 4 to 50 mesh or granular charcoal may, for example, be mentioned, and the aggregates of briquette or shot at a level of from 4 to 20 mesh is preferred.

As alumina, α-alumina, γ-alumina, θ-alumina, etc. differing in the crystalline state may be mentioned. γ-alumina having a relatively large specific surface area is preferred from the viewpoint of realizing a high conversion rate and a high selectivity, and a formed γ-alumina which is γ-alumina formed into spheres or pellets is more preferred from the viewpoint of that the reaction tube is easily packed with the catalyst, and the raw material gas will smoothly flow.

The specific surface area of the carrier is preferably from 10 to 2,000 $m^2/g$, more preferably from 100 to 1,500 $m^2/g$. When the specific surface area of the carrier is at least the above lower limit value, the reactivity of the chloroolefin and hydrogen will further improve. When the specific surface area of the carrier is at most the above upper limit value, the formation of an over-reduced product as a by-product will be further suppressed.

The specific surface area of the carrier is measured by the $N_2$ gas absorption method, for example the method in accordance with the BET method.

<Reaction of Chlorofluoroolefin and Hydrogen>

The reaction of the chlorofluoroolefin and hydrogen may be conducted in a gaseous phase or in a liquid phase.

As the reaction method, the following method (α) or (β) may be mentioned.

Method (α): the chlorofluoroolefin and hydrogen are reacted in a gaseous phase in the presence of the catalyst.

Method (β): the chlorofluoroolefin and hydrogen are reacted in a liquid phase in the presence of the catalyst.

<Method (α)>

The method (α) may, for example, be a method in which the chlorofluoroolefin and hydrogen are introduced to a catalyst layer formed by packing a reactor with the catalyst-supporting carrier and reacted in a gaseous phase. The method may, for example, be specifically a method in which a gas containing a chlorofluoroolefin gas and a hydrogen gas (hereinafter sometimes referred to as "a raw material mixture gas") is introduced to the reactor, followed by reaction.

As the reactor, a known reactor with which the catalyst-supporting carrier can be packed to form a catalyst layer, may be mentioned.

As the reactor, a typical flow reactor used for a gas-solid heterogeneous catalytic reaction in which the catalyst-supporting carrier is a solid and the reaction fluid is a gas may be used. Such a flow reactor is roughly classified into a fixed bed reactor, a moving bed reactor and a fluidized bed reactor.

The fixed bed reactor is a reactor having a catalyst layer in which the catalyst-supporting carrier will not move nor flow. The fixed bed reactor is packed with a formed product of the catalyst-supporting carrier so as to reduce the pressure loss of the reaction fluid. The fixed bed reactor may, for example, be a tubular reactor or a tank reactor. The tubular reactor is preferred in view of control ability of the reaction temperature. The tubular reactor may be a shell and tube heat exchanger comprising many reaction tubes having a small tube diameter arranged in parallel, and a heat medium circulating over the reaction tubes.

The moving bed reactor is a reactor in which the catalyst-supporting carrier is let to move by gravitation and withdrawn from the bottom of the reactor and regenerated.

The fluidized bed reactor is a reactor such that the catalyst-supporting carrier is suspended in the reaction fluid and moves in the reactor. In the fluidized bed reactor, the catalyst layer behaves as if it is a fluid by the reaction fluid.

In the production method of the present invention as the flow reactor, any of the fixed bed reactor, the moving bed reactor and the fluidized bed reactor may be used. As the flow reactor, in order to suppress deterioration of the catalyst without decreasing the selectivity of the catalytic reaction, the fixed bed reactor capable of properly controlling the reaction temperature is preferred.

In any reactor, the number of the catalyst layer may be one, two or more.

The material of the reactor may, for example, be glass, iron, nickel or an alloy containing iron or nickel as the main component.

The catalyst layer is formed by packing the reactor with the catalyst-supporting carrier.

The packing density of the catalyst-supporting carrier in the catalyst layer is from 0.5 to 1 g/cm$^3$, more preferably from 0.6 to 0.8 g/cm$^3$. When the packing density of the catalyst-supporting carrier is at least the lower limit value, the amount of the catalyst-supporting carrier packed per unit volume tends to be large, and the gas amount to be reacted can be increased, whereby the productivity will improve. When the packing density of the catalyst-supporting carrier is at most the upper limit value, the temperature of the catalyst layer will not be too increased as described above, and the after-described maximum temperature of the catalyst layer tends to be maintained at the desired temperature or below.

It is preferred to keep the reaction temperature in the catalyst layer to be a desired temperature so as to maintain a high reactivity. If the reaction temperature in the catalyst layer is low, the reactivity of the catalyst is low. The method to keep the reaction temperature in the catalyst layer to be a desired temperature may, for example, a method of heating the catalyst layer from outside e.g. by a heat medium may be mentioned.

The chlorofluoroolefin and hydrogen react usually in a part of the region of the catalyst layer (hereinafter referred to as "reaction region"). In a case where the reaction temperature in the catalyst layer is kept to be a desired temperature, usually, the temperature on the upstream side in the reaction zone in the catalyst layer is maintained by heating. In this specification, the temperature on the upstream side in the reaction region maintained by heating will be referred to as "the temperature of the catalyst layer".

In the case of the gaseous reaction, the temperature of the catalyst layer is kept to be a temperature higher than the dew point of the raw material mixture gas. For example, in a case where CFO-1214ya having a boiling point of 46° C. is used as the chlorofluoroolefin, considering the reactivity, the temperature of the catalyst layer is preferably at least 50° C., more preferably at least 60° C. Further, in a case where HCFO-1224yd having an estimated boiling point of from 15 to 17° C. is used as the chlorofluoroolefin, the temperature of the catalyst layer is preferably at least 20° C., more preferably at least 30° C.

The catalyst usually deteriorates with time as the reaction proceeds. The reaction zone originates from the introduction part of the raw material mixture gas at the beginning of the reaction. With deterioration of the catalyst at the introduction part of the raw material mixture gas with time as the reaction proceeds, the reaction zone moves toward the downstream side in the gas flow direction.

Since a high temperature produced gas formed in the reaction zone flows into the vicinity on the downstream side in the reaction zone, the vicinity on the downstream side is usually at the highest temperature in the catalyst layer. In this specification, the temperature of the region at the highest temperature in the catalyst layer will be referred to as "the maximum temperature of the catalyst layer". The temperature on the further downstream side of the vicinity on the downstream side decreases from the maximum temperature of the catalyst layer with an increase of the distance from the reaction zone.

As a method of measuring the maximum temperature of the catalyst layer, for example, a measurement method using a bulk thermometer may be mentioned. As described above, since the reaction zone moves toward the downstream side in the gas flow direction, the region indicating the maximum temperature of the catalyst layer also moves together with the movement of the reaction zone. Accordingly, the measurement part of a bulk thermometer is preliminarily disposed in the gas introduction part of the catalyst layer, and after the beginning of the reaction, the measurement part is moved to the downstream side in the gas flow direction as the reaction proceeds, whereby the maximum temperature of the catalyst layer can be measured. In this specification, "the gas introduction part" means a point where the raw material mixture gas is introduced in the catalyst layer.

The maximum temperature of the catalyst layer is preferably at least 90° C., more preferably at least 130° C. When the maximum temperature of the catalyst layer is at least the above lower limit value, the conversion rate can be sufficiently high.

The maximum temperature of the catalyst layer is preferably at most 200° C., more preferably at most 180° C. When the maximum temperature of the catalyst layer is at most the above upper limit value, the excess temperature increase of the catalyst layer due to the heat of the reaction can be suppressed, and the formation of an over-reduced product as a by-product can be suppressed.

As the method of controlling the maximum temperature of the catalyst layer to be a desired temperature, the following methods (α1) to (α3) may, for example, be mentioned.

Method (α1): a method of introducing hydrogen to the catalyst layer dividedly.

Method (α2): a method of making an inert gas flow together with the chlorofluoroolefin and hydrogen in the catalyst layer.

Method (α3): a method of adjusting the temperature of heat medium to heat the reactor to be a lower temperature, setting the dew point of the raw material mixture gas as the lower limit.

Method (α1):

By the method (α1), a high productivity is likely to be maintained while the maximum temperature of the catalyst layer is controlled to at most the desired temperature.

In the method (α1) it is preferred to evenly divide and introduce hydrogen to the respective points, whereby the reaction zone is dispersed and the maximum temperature of the catalyst layer is likely to be kept low.

In the method (α1), the number of hydrogen introduction point is not particularly limited, and may be 2, 3 or more. A case where the number of hydrogen introduction point is 2 may be a case where one point in the gas introduction part from which hydrogen contained in the raw material mixture gas is introduced and one point from which only a hydrogen gas is introduced (hereinafter referred to as "hydrogen introduction part"), i.e. totally 2 points are provided. In view of simplification of the process, the number of the hydrogen introduction point is preferably 2. In order that the reaction zone in the catalyst layer can be dispersed without changing the amount of the chlorofluoroolefin introduced, and that generation of the heat of reaction is prevented from being concentrated in one point, whereby local excessive heat generation in the catalyst layer can be suppressed without decreasing the productivity, the number of the hydrogen introduction point is preferably at least 3.

In a case where the hydrogen introduction part is provided, a method (α1-1) may be mentioned in which a mixture gas of a part of hydrogen and the entire amount of the chlorofluoroolefin to be introduced to the catalyst layer, as the raw material mixture gas, is introduced from the gas introduction part (located on the most upstream side in the gas flow direction) of the catalyst layer, and the rest of hydrogen is introduced from at least one hydrogen introduction part on the downstream side of the gas introduction part. By such a method, in addition to the gas flowing from the upstream side (usually the produced gas after a part of the chlorofluoroolefin is reacted with hydrogen), hydrogen is further introduced from the hydrogen introduction part, and this hydrogen reacts with the unreacted chlorofluoroolefin on the downstream side from the hydrogen introduction part. The produced gas after sufficient reaction of the chlorofluoroolefin and hydrogen is discharged from the gas discharge part located on the most downstream side in the gas flow direction of the catalyst layer.

In the method (α1-1), it is preferred that between the gas introduction part and the first hydrogen introduction part, at least part of hydrogen in the raw material mixture gas is reacted with the chlorofluoroolefin. Further, the hydrogen introduction part on the most downstream side in the gas flow direction is preferably provided at a position such that hydrogen introduced from this hydrogen introduction part can be sufficiently reacted with the unreacted chlorofluoroolefin, in the catalyst layer between this hydrogen introduction part and the gas discharge part.

In a case where at least two catalyst layers are continuously provided in the reactor, as a method of introducing hydrogen, for example, a method may be mentioned in which a part of hydrogen is introduced together with the chlorofluoroolefin from the gas introduction part in the first catalyst layer, and the rest of hydrogen is introduced from the hydrogen filling part of the second or subsequent catalyst layer.

Method (α2):

In the method (α2), by making an inert gas flow and controlling the concentrations of the chlorofluoroolefin and hydrogen flowing in the catalyst layer, the excessive temperature increase of the catalyst layer by the heat of reaction can be suppressed. Further, it is possible to use a diluent gas other than the inert gas instead of the inert gas or together with the inert gas.

The inert gas may, for example, be a nitrogen gas, a rare gas or Freon inert to the hydrogenation reaction. The diluent gas other than the inert gas may, for example, be hydrogen chloride.

The amount of the inert gas introduced to the catalyst layer is preferably at least 0.1 mol, more preferably at least 0.5 mol per 1 mol of the chlorofluoroolefin, whereby the maximum temperature of the catalyst layer is likely to be kept low, the formation of an over-reduced product as a by-product is likely to be suppressed, and the deterioration of the catalyst is likely to be suppressed. The amount of the inert gas introduced is preferably at most 10 mol, more preferably at most 4 mol per 1 mol of the chlorofluoroolefin, in view of the inert gas recovery ratio.

Method (α3):

In the method (α3), by keeping the temperature of the heat medium low, it is possible to more quickly dissipate the heat of reaction, and the excessive temperature increase of the catalyst layer can be suppressed.

As the temperature of the heat medium in the method (α3) is lowered, it is more advantageous to suppress the formation of an over-reduced product. Usually, the temperature of the heat medium is preferably at least +10° C. of the dew point of the chlorofluoroolefin and at most +80° C. of the dew point of the chlorofluoroolefin. In the case of the mixture of CFO-1214ya and CFO-1224yd, the temperature of the heat medium is preferably higher than the dew point and less than 50° C., more preferably higher than dew point and at most 30° C.

As the method for controlling the maximum temperature of the catalyst layer to be the desired temperature, the method (α1), the method (α2) or the method (α3), or the combination of two or three of them is preferred.

The reaction pressure in the method (α) is preferably ordinary pressure in view of the handling efficiency.

The contact time of the chlorofluoroolefin gas to the catalyst in the method (α) is preferably from 4 to 60 seconds, more preferably from 8 to 40 seconds. The contact time is the contact time of the chlorofluoroolefin gas as calculated from the amount of the gas introduced to the reactor and the volume of the catalyst layer.

The proportion of hydrogen to the chlorofluoroolefin in the method (α) is, as represented by the ratio ($H_2$/Cl) of the number of moles of hydrogen to the number of moles of chlorine atoms in the chlorofluoroolefin, preferably at most 0.7, more preferably at most 0.6, further preferably at most 0.5, with a view to suppressing the formation of an over-reduced product as a by-product.

In the method (α), the linear velocity u of the chlorofluoroolefin gas represented by the following formula (8) in the catalyst layer is preferably from 0.1 to 100 cm/sec, more preferably from 1 to 30 cm/sec. This linear velocity u is the linear velocity of the chlorofluoroolefin gas calculated from the amount of the gas introduced to the reactor and the volume of the catalyst layer. When the linear velocity u of the chlorofluoroolefin gas is at least the lower limit value, the productivity will improve. When the linear velocity u of the chlorofluoroolefin gas is at most the upper limit value, the reactivity of the chlorofluoroolefin and hydrogen will improve.

$$u=(W/100)\times V/S \tag{8}$$

wherein W is the concentration (mol %) of the chlorofluoroolefin gas in the entire gas flowing in the catalyst layer, V is the flow rate (cm$^3$/sec) of the entire gas flowing in the catalyst layer, and S is the cross-sectional area (cm$^2$) of the catalyst layer relative to the gas flow direction.

The produced gas after the reaction contains, in addition to the aimed hydrofluoroolefin, unreacted materials, a reaction intermediate and hydrogen chloride.

Hydrogen chloride contained in the produced gas can be removed by blowing the produced gas into an aqueous alkali solution for neutralization. The alkali in the aqueous alkali solution may, for example, be sodium hydroxide or potassium hydroxide.

As a method for separating the hydrofluoroolefin and the unreacted chlorofluoroolefin from the produced gas, for example, a known method such as distillation may be employed.

The chlorofluoroolefin separated from the produced gas can be recycled. For example, separated HCFO-1224yd may be reacted with hydrogen as the chlorofluoroolefin together with CFO-1214ya, or only HCFO-1224yd may be reacted with hydrogen independently from CFO-1214ya.

In a case where a mixture of CFO-1214ya and HCFO-1224yd is used as the chlorofluoroolefin, since HCFO-1224yd is an intermediate when HFO-1234yf is obtained from CFO-1214ya, usually, a mixture with a low proportion of HCFO-1224yd is used. Accordingly, the proportion of HCFO-1224yd based on 100 mol % in total of CFO-1214ya and HCFO-1224yd is preferably at most 50 mol %, more preferably at most 25 mol %.

<Method (β)>

In the method (β), a medium is preferably used. The medium may, for example, be water or an organic solvent such as an alcohol.

The amount of the medium used is preferably from 10 to 100 parts by mass per 100 parts by mass of the chlorofluoroolefin.

As a method of supplying hydrogen, a method of blowing a hydrogen gas to a liquid containing the catalyst and the chlorofluoroolefin and the medium used as the case requires, or a method of adding a medium having hydrogen preliminarily dissolved by pressurization to a liquid containing the catalyst and the chlorofluoroolefin may, for example, be mentioned.

The reaction of the chlorofluoroolefin and hydrogen in the method (β) may be conducted by batch or continuously.

The reaction temperature in the method (β) is preferably from 0 to 150° C., more preferably from 20 to 100° C. When the reaction temperature is at least the lower limit value, the reactivity of the chlorofluoroolefin and hydrogen will improve. When the reaction temperature is at most 150° C., the formation of an over-reduced product as a by-product is likely to be suppressed.

The reaction pressure in the method (β) is preferably from 0.01 to 5 MPaG, more preferably from 0.1 to 1 MPaG by the gauge pressure.

The reaction time in the method (β) is preferably from 1 to 50 hours in the case of the batch reaction, and is preferably from 1 to 60 seconds in the case of the continuous reaction.

The amount of hydrogen supplied in the method (β) is such that the ratio (H$_2$/Cl) of the number of moles of hydrogen to the number of moles of chlorine atoms in the chlorofluoroolefin is preferably at most 0.7, more preferably at most 0.6, further preferably at most 0.5, whereby the formation of an over-reduced product as a by-product is likely to be suppressed. Further, the ratio (H$_2$/Cl) is preferably at least 0.1, more preferably at least 0.2, in view of the yield of the aimed product. The amount of hydrogen supplied means the amount of hydrogen dissolved in the reaction liquid.

The reaction liquid after the reaction contains, in addition to the aimed hydrofluoroolefin, unreacted materials, a reaction intermediate and hydrogen chloride.

Hydrogen chloride contained in the reaction liquid can be removed by neutralization by addition of an alkali to the reaction liquid. The alkali may, for example, be sodium hydroxide or potassium hydroxide. The alkali may be preliminarily added to the reaction liquid used for the reaction.

As a method of separating the hydrofluoroolefin and the unreacted chlorofluoroolefin from the reaction liquid, for example, a known method such as distillation may be employed.

The chlorofluoroolefin separated from the reaction liquid can be recycled. For example, HCFO-1224yd separated may be reacted with hydrogen as the chlorofluoroolefin together with CFO-1214ya, or only HCFO-1224yd separated from CFO-1214ya may be reacted with hydrogen.

As the reactor used in the method (β), a known reactor in which the reaction materials can be brought into contact with each other and are subjected to a liquid phase reaction in the presence of the catalyst may be mentioned.

The material of the reactor may, for example, be glass, iron, nickel or an alloy containing iron or nickel as the main component.

(Function and Mechanism)

In the above described method for producing a hydrofluoroolefin of the present invention, an over-reduced product is less likely to be formed as a by-product. As a result, the selectivity of the aimed product can be improved. Thus, according to the production method of the present invention, a high purity hydrofluoroolefin can be efficiently produced, in which the concentration of an over-reduced product is low.

The mechanism that an over-reduced product is less likely to be formed as a by-product, is considered as described below.

The ability of metals such as the platinum group metal and gold to chemically absorb hydrogen varies depending on elements (New Chemical of Catalysts, second edition, SANKYO SHUPPAN Co., Ltd., "absorption ability of metal" at p. 181, Table 8-1). In the catalytic reaction conducted on the surface of the platinum group metal, whether hydrogen is readily absorbed or not to the surface influences the catalytic activity.

The ability of gold to chemically absorb hydrogen is less than the Pd/Pt metal. Thus, it is considered that when the Pd/Pt metal is alloyed with gold, the hydrogen absorption ability of the Pd/Pt metal on its surface deteriorates. The hydrogen absorption ability of the Pd/Pt metal on its surface deteriorates, whereby the catalytic activity of the Pd/Pt metal becomes low. As the result, the excessive hydrogen reduction activity by the Pd/Pt metal can be reduced, whereby the selectivity of the aimed product improves, and the formation of an over-reduced product as a by-product is suppressed. Further, the proportion of gold at the surface of the alloy particles is from 5 to 30 mass %, whereby the effect to suppress the formation of an over-reduced product as a by-product by gold can be sufficiently secured, and a high conversion rate by the Pd/Pt metal can be also secured.

EXAMPLES

Now, the present invention will be described in further detail with reference to Examples. However, the present invention is by no means restricted to such specific Examples.

Examples 1 to 11 are working examples, and Examples 12 to 14 are Comparative Examples.

(Measurement of Proportion of Gold at Surface of Alloy Particles)

The proportion of gold was measured by the XPS measurement. In the XPS measurement, the peak position of the bonding energy of 3d5/2 electron orbit in a palladium atom is from 335.1 to 335.4 eV, the peak position of the bonding energy of 4f7/2 electron orbit in a platinum atom is from 71.0 to 71.2 eV, and the peak position of the bonding energy of 4f7/2 electron orbit in a gold atom is from 83.8 to 84.2 eV. The proportion of gold at the surface of the alloy particles was calculated from the peak intensity ratio of these peak positions.

The XPS measurement was carried out by using a X-ray photoelectron analytical apparatus (QuanteraSXM, manufactured by ULVAC-PHI, Inc. under the following conditions.

X-Ray source: AlKα ray monochromatized by a monochromer

Output power: 40 W

Measured area: 800 μm×300 μm

Path energy: Wide scan: 117.4 eV (0.50 eV/Step), narrow scan: 55.0 eV (0.05 eV/Step), Electrostatic charge neutralization gun: dual beam method simultaneously applying low energy electron beam and Ar ion beam Take off angle: 45°

(Conversion Rate of CFO-1214ya)

The conversion rate X (%) of CFO-1214ya was obtained by the following formula:

$$X=[Xa-Xb]/Xa]\times 100$$

wherein Xa is the proportion (mol %) of CFO-1214ya in the material mixed gas, and Xb is the proportion (mol %) of CFO-1214ya in the formed gas.

(Production of CFO-1214ya)

CFO-1214ya was produced by using HCFC-225 ("ASAHIKLIN (registered trademark) AK225", manufactured by Asahi Glass Company, Limited) as raw material by the following method.

Into a glass reactor having an internal capacity of 1 L equipped with a Dimroth condenser cooled to 0° C., 3 g of TBAB as a phase transfer catalyst, 83 g (1.485 mol) of potassium hydroxide, 180 g of water and 609 g (3.0 mol) of HCFC-225 were charged. The mixture was gradually heated with stirring and reacted at 45° C. for 1 hour. A reaction crude liquid separated into an organic phase and an aqueous phase was subjected to liquid separation, and the organic phase was subjected to distillation by a distillation column (capacity: 1 L and the number of theoretical plate: 10). As a result of the distillation, 262 g (1.43 mol) of CFO-1214ya (boiling point: 45° C.) with a purity of 99.5% was obtained.

Example 1

0.5 Part by mass of palladium and gold particles (palladium:gold=90:10 (mass ratio)) was supported on 100 parts by mass of activated carbon (BET specific surface area: 1,100 m²/g), followed by heat treatment at 500° C. for 3 hours under flowing nitrogen gas to form an alloy, whereby palladium-gold alloy particles (the proportion of gold at the surface of the alloy particles: 12.2 mass %)-supporting activated carbon (hereinafter referred to also as "Pd—Au/C") was prepared.

For preparation of HFO-1234 yf, a reaction apparatus 101 shown in the Figure was used.

The reaction apparatus 101 comprises two reaction tubes 110A and 110B, and a salt bath 130 in which the tubes are dipped. The reaction tube 110A has two catalyst packing parts 113a and 114a on the inlet 111a side and on the outlet 112a side. Likewise, the reaction tube 110B has two catalyst packing parts 113b and 114b on the inlet 111b side and on the outlet 112b side. The outlet 112a of the reaction tube 110A and the inlet 111b of the reaction tube 110B are connected by piping.

As each of the reaction tubes 110A and 110B, a reaction tube made of Inconel (registered trademark) 600 having an inner diameter of 2.54 cm and a length of 100 cm was used. Further, the catalyst packing part 114a on the outlet 112a side of the reaction tube 110A was packed with Pd—Au/C to form a catalyst layer 120A having a height of 40 cm. Likewise, the catalyst packing parts 113b and 114b on the inlet 111b side and on the outlet 112b side of the reaction tube 110B were respectively packed with Pd—Au/C to form catalyst layers 120B and 120C each having a height of 40 cm. The packing density of Pd—Au/C in each of the catalyst layers 120A to 120C was 0.73 g/cm³.

The reaction tubes 110A and 110B were dipped in the salt bath 130 so that the catalyst layers 120A to 120C were entirely dipped, and the catalyst layers 120A to 120C were heated to 80° C.

The chlorofluoroolefin gas (A) composed of CFO-1214ya, a hydrogen gas (B) and a nitrogen gas (C) were made to flow through the reaction tubes 110A and 110B so that the total molar ratio would be hydrogen/CFO-1214ya/nitrogen=1/1/2. The contact time of the chlorofluoroolefin gas (A) to the catalyst layers 120A to 120C was 18 seconds, and the linear velocity u of the chlorofluoroolefin gas (A) was 7 cm/sec.

Further, 50% of the hydrogen gas (B) was introduced together with the chlorofluoroolefin gas (A) from the inlet 111a of the reaction tube 110A, and the rest was introduced to a piping portion connecting the reaction tube 110A and the reaction tube 110B. That is, the hydrogen gas (B) was introduced as divided into the catalyst layer 120A (at 0 cm point) and the catalyst layer 120B (at 40 cm point) in a catalyst layer (catalyst layer length: 120 cm) consisting of the catalyst layers 120A to 120C.

The maximum temperatures of the catalyst layers 120A, 120B and 120C during the reaction were measured respectively by bulk thermometers 140A to 140C inserted to the respective catalyst layers.

A produced gas (D) discharged from the outlet 112b of the reaction tube 110B of the reaction apparatus 101 was analyzed by gas chromatography (hereinafter referred to as "GC"). Results are shown in Table 1.

Example 2

0.5 Part by mass of palladium and gold (palladium:gold=90:10 (mass ratio)) was supported on 100 parts by mass of activated carbon (BET specific surface area: 1,100 m$^2$/g), followed by heat treatment at 500° C. for 3 hours under flowing nitrogen gas to form an alloy, whereby a palladium-gold alloy particles (the proportion of gold at the surface of the alloy particles: 19.4 mass %)-supporting activated carbon (hereinafter referred to also as "Pd—Au/C") was prepared.

HFO-1234yf was produced in the same manner as in Example 1, except that the Pd—Au/C in Example 2 was used, instead of the Pd—Au/C in Example 1.

The formed gas (D) was analyzed by GC. Results are shown in Table 1.

Example 3

0.5 Part by mass of palladium and gold (palladium:gold=90:10 (mass ratio)) was supported on 100 parts by mass of activated carbon (BET specific surface area: 1,100 m$^2$/g), followed by heat treatment at 500° C. for 3 hours under flowing nitrogen gas to form an alloy, whereby a palladium-gold alloy particles (the proportion of gold at the surface of the alloy particles: 19.3 mass %)-supporting activated carbon (hereinafter referred to also as "Pd—Au/C") was prepared.

HFO-1234yf was produced in the same manner as in Example 1, except that the Pd—Au/C in Example 3 was used, instead of the Pd—Au/C in Example 1.

The formed gas (D) was analyzed by GC. Results are shown in Table 1.

Example 4

0.5 Part by mass of palladium and gold (palladium:gold=90:10 (mass ratio)) was supported on 100 parts by mass of activated carbon (BET specific surface area: 1,100 m$^2$/g), followed by heat treatment at 480° C. for 3 hours under flowing nitrogen gas to form an alloy, whereby a palladium-gold alloy particles (the proportion of gold at the surface of the alloy particles: 9.4 mass %)-supporting activated carbon (hereinafter referred to also as "Pd—Au/C") was prepared.

HFO-1234yf was produced in the same manner as in Example 1, except that the Pd—Au/C in Example 4 was used, instead of the Pd—Au/C in Example 1.

The formed gas (D) was analyzed by GC. Results are shown in Table 1.

Example 5

0.5 Part by mass of palladium and gold (palladium:gold=90:10 (mass ratio)) was supported on 100 parts by mass of activated carbon (BET specific surface area: 1,100 m$^2$/g), followed by heat treatment at 480° C. for 3 hours under flowing nitrogen gas to form an alloy, whereby a palladium-gold alloy particles (the proportion of gold at the surface of the alloy particles: 8.6 mass %)-supporting activated carbon (hereinafter referred to also as "Pd—Au/C") was prepared.

HFO-1234yf was produced in the same manner as in Example 1, except that the Pd—Au/C in Example 5 was used, instead of the Pd—Au/C in Example 1.

The formed gas (D) was analyzed by GC. Results are shown in Table 1.

Example 6

0.5 Part by mass of palladium and gold particles (palladium:gold=90:10 (mass ratio)) was supported on 100 parts by mass of activated carbon (BET specific surface area: 1,100 m$^2$/g), followed by heat treatment at 460° C. for 3 hours under flowing nitrogen gas to form an alloy, whereby a palladium-gold alloy particles (the proportion of gold at the surface of the alloy particles: 14.1 mass %)-supporting activated carbon (hereinafter referred to also as "Pd—Au/C") was prepared.

HFO-1234yf was produced in the same manner as in Example 1, except that the Pd—Au/C in Example 6 was used, instead of the Pd—Au/C in Example 1.

The formed gas (D) was analyzed by GC. Results are shown in Table 1.

Example 7

0.5 Part by mass of palladium and gold (palladium:gold=90:10 (mass ratio)) was supported on 100 parts by mass of activated carbon (BET specific surface area: 1,100 m$^2$/g), followed by heat treatment at 460° C. for 3 hours under flowing nitrogen gas to form an alloy, whereby a palladium-gold alloy particles (the proportion of gold at the surface of the alloy particles: 11.8 mass %)-supporting activated carbon (hereinafter referred to also as "Pd—Au/C") was prepared.

HFO-1234yf was produced in the same manner as in Example 1, except that the Pd—Au/C in Example 7 was used, instead of the Pd—Au/C in Example 1.

The formed gas (D) was analyzed by GC. Results are shown in Table 1.

Example 8

0.5 Part by mass of palladium and gold (palladium:gold=90:10 (mass ratio)) was supported on 100 parts by mass of activated carbon (BET specific surface area: 1,100 m$^2$/g), followed by heat treatment at 460° C. for 3 hours under flowing nitrogen gas to form an alloy, whereby a palladium-gold alloy particles (the proportion of gold at the surface of the alloy particles: 16.8 mass %)-supporting activated carbon (hereinafter referred to also as "Pd—Au/C") was prepared.

HFO-1234yf was produced in the same manner as in Example 1, except that the Pd—Au/C in Example 8 was used, instead of the Pd—Au/C in Example 1.

The formed gas (D) was analyzed by GC. Results are shown in Table 1.

Example 9

Pd—Au/C having 0.5 part by mass of palladium-gold particles (palladium:gold=90:10 (mass ratio), the proportion of gold at the surface of the alloy particles: 5.0 mass %) supported on 100 parts by mass of activated carbon (BET specific surface area: 1,100 m$^2$/g), was prepared.

HFO-1234yf was produced in the same manner as in Example 1, except that the Pd—Au/C in Example 9 was used, instead of the Pd—Au/C in Example 1.

The formed gas (D) was analyzed by GC. Results are shown in Table 1.

Example 10

0.5 Part by mass of palladium and gold (palladium:gold=90:10 (mass ratio)) was supported on 100 parts by mass of activated carbon (BET specific surface area: 1,100 m$^2$/g), followed by heat treatment at 460° C. for 3 hours under flowing nitrogen gas to form an alloy, whereby a palladium-gold alloy particles (the proportion of gold at the surface of the alloy particles: 24.4 mass %)-supporting activated carbon (hereinafter referred to also as "Pd—Au/C") was prepared.

HFO-1234yf was produced in the same manner as in Example 1, except that the Pd—Au/C in Example 10 was used, instead of the Pd—Au/C in Example 1.

The formed gas (D) was analyzed by GC. Results are shown in Table 1.

Example 11

Pd—Au/C having 0.5 part by mass of palladium-gold particles (palladium:gold=68.4:31.6 (mass ratio), the proportion of gold at the surface of the alloy particles: 17.5 mass %) supported on 100 parts by mass of activated carbon (BET specific surface area: 1,100 m$^2$/g), was prepared.

HFO-1234yf was produced in the same manner as in Example 1, except that the Pd—Au/C in Example 11 was used, instead of the Pd—Au/C in Example 1.

of gold at the surface of the alloy particles: 4.5 mass %) supported on 100 parts by mass of activated carbon (BET specific surface area: 1,100 m$^2$/g) was prepared.

HFO-1234yf was produced in the same manner as in Example 1, except that the Pd—Au/C in Example 13 was used, instead of the Pd—Au/C in Example 1.

The formed gas (D) was analyzed by GC. Results are shown in Table 1.

Example 14

0.5 Part by mass of palladium and gold (palladium:gold=68.4:31.6 (mass ratio)) was supported on 100 parts by mass of activated carbon (BET specific surface area: 1,100 m$^2$/g), followed by heat treatment at 500° C. for 3 hours under flowing nitrogen gas to form an alloy, whereby a palladium-gold alloy particles (the proportion of gold at the surface of the alloy particles: 45.3 mass %)-supporting activated carbon (hereinafter referred to also as "Pd—Au/C") was prepared.

HFO-1234yf was produced in the same manner as in Example 1, except that the Pd—Au/C in Example 14 was used, instead of the Pd—Au/C in Example 1.

The formed gas (D) was analyzed by GC. Results are shown in Table 1.

TABLE 1

| Ex. | Catalyst-supporting carrier | Amount of alloy particles supported (parts by mass) | Mass ratio of Pd/Pt metal to gold at alloy particles | Proportion of gold at surface of alloy particles (mass %) | Maximum temperature of catalyst layer (° C.) | Conversion rate (%) CFO-1214ya | Content of HFC-254eb in formed gas (vol %) | Content of HFO-1243zf to HFO-1234yf in formed gas (vol ppm) |
|---|---|---|---|---|---|---|---|---|
| 1 | Pd—Au/C | 0.5 | 90:10 | 12.2 | 166.4 | 55.1 | 5.5 | 285 |
| 2 | Pd—Au/C | 0.5 | 90:10 | 19.4 | 150.0 | 53.2 | 7.2 | 274 |
| 3 | Pd—Au/C | 0.5 | 90:10 | 19.3 | 156.6 | 52.2 | 8.8 | 512 |
| 4 | Pd—Au/C | 0.5 | 90:10 | 9.4 | 150.0 | 51.5 | 5.9 | 480 |
| 5 | Pd—Au/C | 0.5 | 90:10 | 8.6 | 157.8 | 54.4 | 6.3 | 216 |
| 6 | Pd—Au/C | 0.5 | 90:10 | 14.1 | 155.8 | 52.3 | 7.6 | 77 |
| 7 | Pd—Au/C | 0.5 | 90:10 | 11.8 | 161.6 | 50.5 | 6.0 | 375 |
| 8 | Pd—Au/C | 0.5 | 90:10 | 16.8 | 158.6 | 52.0 | 6.6 | 282 |
| 9 | Pd—Au/C | 0.5 | 90:10 | 5.0 | 50.4 | 20.8 | 9.2 | <10 |
| 10 | Pd—Au/C | 0.5 | 90:10 | 24.4 | 48.7 | 14.2 | 3.2 | <10 |
| 11 | Pd—Au/C | 0.5 | 68.4:31.6 | 17.5 | 99.7 | 44.3 | 9.8 | 34 |
| 12 | Pd/C | 0.5 | 100:0 | 0 | 16.03 | 51.5 | 10.2 | 1220 |
| 13 | Pd—Au/C | 0.5 | 90:10 | 4.5 | 160.0 | 49.3 | 14.0 | 8154 |
| 14 | Pd—Au/C | 0.5 | 68.4:31.6 | 45.3 | 52.4 | 31.7 | 18.9 | <10 |

The formed gas (D) was analyzed by GC. Results are shown in Table 1.

Example 12

Palladium-supporting activated carbon (hereinafter referred to as "Pd/C") having 0.5 part by mass of palladium particles supported on 100 parts by mass of activated carbon (BET specific surface area: 1,100 m$^2$/g) was prepared.

HFO-1234yf was produced in the same manner as in Example 1, except that the Pd—Au/C in Example 12 was used, instead of the Pd—Au/C in Example 1.

The formed gas (D) was analyzed by GC. Results are shown in Table 1.

Example 13

Pd—Au/C having 0.5 part by mass of palladium-gold particles (palladium:gold=90:10 (mass ratio), the proportion It is evident from Table 1 that the formation of HFC-254eb and HFO-1243zf as over-reduced products in Examples 1 to 11 where the catalyst-supporting carrier having palladium-gold alloy particles supported on active carbon wherein the proportion of gold at the surface of the alloy particles was from 5 to 30 mass % was used, was less than in Example 12 where the catalyst-supporting carrier having palladium supported on active carbon was used and in Example 13 where the catalyst-supporting carrier having palladium-gold alloy particles supported on active carbon wherein the proportion of gold at the surface of the alloy particles is less than 5 mass % was used. Further, the formation of HFC-254eb as an over-reduced product in Examples 1 to 11 was less than in Example 14 where the catalyst-supporting carrier having palladium-gold alloy particles supported on active carbon wherein the proportion of gold at the surface of the alloy particles exceeded 30 mass % was used.

INDUSTRIAL APPLICABILITY

A hydrofluoroolefin obtained by the production method of the present invention has high purity with the formation of an over-reduced product as a by-product suppressed. Accordingly, the obtained hydrofluoroolefin can be used as e.g. a refrigerant which replaces freon such as a chlorofluorocarbon without any purification and separation means, etc.

This application is a continuation of PCT Application No. PCT/JP2015/083811, filed on Dec. 1, 2015, which is based upon and claims the benefit of priority from Japanese Patent Application No. 2014-246810 filed on Dec. 5, 2014. The contents of those applications are incorporated herein by reference in their entireties.

REFERENCE SYMBOLS

101: Reaction apparatus, 110A: reaction tube, 110B: Reaction tube, 111a: inlet, 111b: inlet, 112a: outlet, 112b: outlet, 113a: catalyst packing part, 113b: catalyst packing part, 114a: catalyst packing part, 114b: catalyst packing part, 120A: catalyst layer, 120B: catalyst layer, 120C: catalyst layer, 130: salt bath, 140A: thermometer, 140B: thermometer, 140C: thermometer, A: chlorofluoroolefin gas, B: hydrogen gas, C: nitrogen gas, D: formed gas.

What is claimed is:

1. A method for producing 2,3,3,3-tetrafluoropropene, the method comprising:
    reacting 1,1-dichloro-2,3,3,3-tetrafluoropropene with hydrogen in the presence of a catalyst supported on a carrier, to obtain 2,3,3,3-tetrafluoropropene,
    wherein the catalyst comprises alloy particles comprising at least one platinum group metal selected from the group consisting of palladium and platinum, and gold,
    the proportion of the gold at the surface of the alloy particles is from 8.6 to 19.4 mass % per 100 mass % in total of the platinum group metal and the gold at the surface of the alloy particles,
    the 1,1-dichloro-2,3,3,3-tetrafluoropropene and the hydrogen are introduced to a catalyst layer packed with the carrier supporting the catalyst, and
    the temperature of the region at the highest temperature in the catalyst layer is from 99.7° C. to 166.4° C.

2. The method for producing 2,3,3,3-tetrafluoropropene according to claim 1, wherein the proportion of the gold at the surface of the alloy particles is from 8.6 to 15 mass % per 100 mass % in total of the platinum group metal and the gold at the surface of the alloy particles.

3. The method for producing 2,3,3,3-tetrafluoropropene according to claim 1, wherein the catalyst comprises alloy particles of a palladium-gold alloy.

4. The method for producing 2,3,3,3-tetrafluoropropene according to claim 1, wherein the carrier is at least one member selected from the group consisting of activated carbon, carbon black and carbon fibers.

5. The method for producing 2,3,3,3-tetrafluoropropene according to claim 1, wherein the carrier is activated carbon.

6. The method for producing 2,3,3,3-tetrafluoropropene according to claim 1, wherein the carrier is at least one member selected from the group consisting of alumina, silica, titania and zirconia.

7. The method for producing 2,3,3,3-tetrafluoropropene according to claim 1, wherein the amount of the alloy particles supported is from 0.1 to 10 parts by mass based on 100 parts by mass of the carrier.

8. The method for producing 2,3,3,3-tetrafluoropropene according to claim 1, wherein the 1,1-dichloro-2,3,3,3-tetrafluoropropene and hydrogen are reacted in a gaseous phase.

9. The method for producing 2,3,3,3-tetrafluoropropene according to claim 8, wherein the 1,1-dichloro-2,3,3,3-tetrafluoropropene and hydrogen are introduced to a gas introduction part of the catalyst layer, and, at the same time, hydrogen is introduced from at least one point between the gas introduction part and a gas discharge part of the catalyst layer.

10. The method for producing 2,3,3,3-tetrafluoropropene according to claim 1, wherein the 1,1-dichloro-2,3,3,3-tetrafluoropropene and hydrogen are reacted in a liquid phase in the presence of the carrier supporting the catalyst.

11. A method for producing a hydrofluoroolefin, the method comprising:
    reacting a chlorofluoroolefin of formula (1) with hydrogen in the presence of a catalyst supported on a carrier, to obtain a hydrofluoroolefin of formula (2),
    wherein the catalyst comprises alloy particles comprising at least one platinum group metal selected from the group consisting of palladium and platinum, and gold,
    the proportion of the gold at the surface of the alloy particles is from 8.6 to 19.4 mass % per 100 mass % in total of the platinum group metal and the gold at the surface of the alloy particles, and
    the reacting of the chlorofluoroolefin is conducted by at least one method selected from the group consisting of: a method of dividedly introducing hydrogen to a catalyst layer which is packed with the carrier supporting the catalyst; a method of flowing an inert gas together with the chlorofluoroolefin and hydrogen in the catalyst layer; and a method of setting the temperature of a heat medium to at least 10° C. higher than and at most 80° C. higher than the dew point of the chlorofluoroolefin, and
    the temperature of the region at the highest temperature in the catalyst layer is from 99.7° C. to 166.4° C.:

$$CZX=CClY \qquad (1)$$

wherein X is a fluorine atom or a chlorine atom, Y is a fluorine atom, a chlorine atom or a hydrogen atom, and Z is a fluorine atom or $CF_3$;

$$CZX'=CHY' \qquad (2)$$

wherein X' is a fluorine atom when X is a fluorine atom, or X' is a hydrogen atom when X is a chlorine atom, Y' is a fluorine atom when Y is a fluorine atom, or Y' is a hydrogen atom when Y is a chlorine atom or a hydrogen atom, and Z is the same as Z in the formula (1).

12. The method for producing a hydrofluoroolefin according to claim 11, wherein the reacting of the chlorofluoroolefin is conducted by at least one method selected from the group consisting of: a method of dividedly introducing hydrogen to the catalyst layer; and a method of setting the temperature of the heat medium to at least 10° C. higher than and at most 80° C. higher than the dew point of the chlorofluoroolefin.

13. The method for producing a hydrofluoroolefin according to claim 11, wherein the proportion of the gold at the surface of the alloy particles is from 8.6 to 15 mass % per 100 mass % in total of the platinum group metal and the gold at the surface of the alloy particles.

14. The method for producing a hydrofluoroolefin according to claim 11, wherein the catalyst comprises alloy particles of a palladium-gold alloy.

15. The method for producing a hydrofluoroolefin according to claim 11, wherein the carrier is activated carbon.

16. The method for producing a hydrofluoroolefin according to claim 11, wherein the carrier is at least one member selected from the group consisting of alumina, silica, titania and zirconia.

17. The method for producing a hydrofluoroolefin according to claim 11, wherein the amount of the alloy particles supported is from 0.1 to 10 parts by mass based on 100 parts by mass of the carrier.

18. The method for producing a hydrofluoroolefin according to claim 11, wherein the chlorofluoroolefin and hydrogen are introduced to a gas introduction part of the catalyst layer, and, at the same time, hydrogen is introduced from at least one point between the gas introduction part and a gas discharge part of the catalyst layer.

19. The method for producing a hydrofluoroolefin according to claim 11, wherein the ratio ($H_2$/Cl) of the number of moles of hydrogen to the number of moles of chlorine atoms in the chlorofluoroolefin is from 0.1 to 0.7.

20. The method for producing a hydrofluoroolefin according to claim 11, wherein the chlorofluoroolefin is 1,1-dichloro-2,3,3,3-tetrafluoropropene, and the hydrofluoroolefin is 2,3,3,3-tetrafluoropropene.

* * * * *